United States Patent [19]

Wagstaff

[11] 4,288,645

[45] Sep. 8, 1981

[54] PROCESS FOR THE PREPARATION OF AROMATIC HYDROCARBONS AND HYDROGEN FROM PROPANE

[75] Inventor: Nigel Wagstaff, Amsterdam, Netherlands

[73] Assignee: Shell Oil Company, Houston, Tex.

[21] Appl. No.: 125,734

[22] Filed: Feb. 28, 1980

[30] Foreign Application Priority Data

Mar. 14, 1979 [NL]  Netherlands ......................... 7902020

[51] Int. Cl.³ ........................ C07C 2/76; C07C 15/02
[52] U.S. Cl. ..................................... 585/415; 208/135
[58] Field of Search ......................... 585/415; 208/135

[56] References Cited

U.S. PATENT DOCUMENTS

| | | | |
|---|---|---|---|
| 3,760,024 | 9/1973 | Cattanach | 585/415 |
| 3,845,150 | 10/1974 | Yan et al. | 208/135 |
| 4,180,689 | 12/1979 | Davies et al. | 585/407 |

*Primary Examiner*—Delbert E. Gantz
*Assistant Examiner*—G. E. Schmitkons
*Attorney, Agent, or Firm*—Ronald R. Reper

[57] ABSTRACT

A process is disclosed for the preparation of an aromatic hydrocarbon mixture and hydrogen from a light hydrocarbon stream containing at least 50% w propane using as catalyst certain crystalline silicates promoted with zinc.

5 Claims, No Drawings

PROCESS FOR THE PREPARATION OF AROMATIC HYDROCARBONS AND HYDROGEN FROM PROPANE

The invention relates to a process for the preparation of aromatic hydrocarbons and hydrogen from propane or from a hydrocarbon mixture which consists of more than 75% w paraffins with at most four carbon atoms in the molecule ($C_4$-paraffins) and of at least 50% w propane, using a crystalline silicate as the catalyst.

In an investigation by the Applicant concerning the above-mentioned process it has been found that the activity, the aromatics selectivity and the hydrogen selectivity of these catalysts are in the first place greatly dependent on the value of y in the formula which gives the overall composition of the silicate, and further on the pressure used in the process. It was found that to reach an activity, an aromatics selectivity and a hydrogen selectivity which are acceptable for commercial use of the process, y should be at least 0.0065, the silicate should contain zinc as the promoter and the process should be carried out at a pressure between 5 and 10 bar.

SUMMARY OF THE INVENTION

The present invention therefore relates to a process for the preparation of aromatic hydrocarbons and hydrogen, in which propane or a hydrocarbon mixture which consists of more than 75% w $C_4$-paraffins and at least 50% w propane is contacted at an elevated temperature and a pressure of between 5 and 10 bar with a crystalline silicate as hereinafter defined, in which the formula which gives the overall composition of the silicate, the value of y is at least 0.0065 and the silicate contains zinc as the promotor.

DESCRIPTION OF PREFERRED EMBODIMENTS

In the process according to the invention the starting material should be propane or a hydrocarbon mixture which consists of more than 75% w $C_4$-paraffins and at least 50% w propane. Suitable $C_4$-paraffins are methane, ethane, propane, butane and isobutane. If the starting material is a hydrocarbon mixture which comprises in addition to one or more $C_4$-paraffins one or more other hydrocarbons, these other hydrocarbons may be, inter alia, monoolefins, diolefins or $C_5$-paraffins. The preferred starting material is a hydrocarbon mixture consisting of more than 60% w propane. It is also preferred to use hydrocarbon mixtures consisting of less than 20% w methane and/or ethane. A very suitable feed for the present process is a hydrocarbon mixture consisting substantially of $C_3$ and $C_4$ paraffins which has been obtained as a by-product in mineral oil production.

The process according to the invention is preferably carried out at a temperature of from 400° to 700° C. and particularly from 450° to 600° C., a pressure of from 6 to 9 bar and a space velocity of from 0.1 to 20 g.g.$^{-1}$.h$^{-1}$ and particularly from 0.5 to 10 g.g$^{-1}$.h$^{-1}$.

In the process according to the invention propane or a hydrocarbon mixture which consists of more than 75% w $C_4$-paraffins and at least 50% w propane is converted into aromatic hydrocarbons and hydrogen by contacting this feed with a certain crystalline silicate. These crystalline silicates are characterized in that ater 1 hour's calcining in air at 500° C. they have the following properties:

(a) thermally stable up to a temperature above 600° C., (b) an X-ray powder diffraction pattern showing, inter alia, the reflections given in Table A.

TABLE A

| Radiation: Cu-K $2\theta$ | Wavelength 0.15418 nm relative intensity |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M |

(c) after conversion of the silicate into the H-form and after evacuation at $2\times10^{-9}$ bar and 400° C. for 16 hours and measured at a hydrocarbon pressure of $8\times10^{-2}$ bar and 100° C., the adsorption of n-hexane is at least 0.8 mmol/g, the adsorption of 2,2-dimethylbutane at least 0.5 mmol/g and the ratio $$\frac{\text{adsorption of n-hexane}}{\text{adsorption of 2,2-dimethylbutane}}$$

at least 1.5, (d) the composition, expressed in moles of the oxides, is as follows:

$y.(1.0\times0.3)M_{n/2}O.y. Al_2O_3.SiO_2$, wherein M=H and/or alkali metal and/or alkaline-earth metal, n is the valency of M and $0<y\leq0.1$.

For the adsorption measurements mentioned under (c) the silicate should first be converted into the H-form. This conversion is effected by boiling the silicate calcined at 500° C. with 1.0 molar $NH_4NO_3$ solution, washing with water, boiling again with 1.0 molar $NH_4NO_3$ solution and washing, drying at 120° C. and calcining at 500° C. The complete X-ray powder diffraction pattern of a typical example of a silicate suitable for use according to the invention is shown in Table B (radiation: Cu-K; wavelength: 0.15418 nm).

TABLE B

| $2\theta$ | relative intensity (100. I:Io) | description |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100* | SP |
| 23.95 | 45 | SP |
| 24.40 | 27 | SP |

TABLE B-continued

| 2 θ | relative intensity (100. I:Io) | description |
|---|---|---|
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

*Io = intensity of the strongest separate reflection present in the pattern.

The letters used in Table B for describing the reflections have the following meanings: SP=sharp; SR=shoulder; NL=normal; BD=broad; θ=angle according to Bragg's law.

The crystalline silicates which are used as the catalyst in the process according to the invention can be prepared starting from an aqueous mixture containing the following compounds: one or more compounds of an alkali- or akaline-earth metal (M), one or more compounds containing an organic cation (R) or from which such a cation is formed during the preparation of the silicate, one or more silicon compounds and one or more aluminum compounds. Exemplary organic cations include, e.g., primary, secondary and tertiary alkyl amines and quaternary ammonium hydroxide. The preparation is performed by maintaining the mixture at elevated temperature until the silicate has been formed and, subsequently, separating the crystals of the silicate from the mother liquor. In the aqueous mixture from which the silicates are prepared, the various compounds should be present in the following ratio, expressed in moles of the oxides:

$M_{2/n}O:(R)_{2/p}O = 0.1-20$,
$(R)_{2/p}O:SiO_2 = 0.01-0.5$,
$SiO_2:Al_2O_3 - 300$,
$H_2O:SiO_2 = 5-50$;

n is the valency of M and p is the valency of R.

In the preparation of the silicates it is preferred to start from the base mixture in which M is present in a sodium compound and R in a tetrapropylammonium compound.

The value of y in the formula which gives the composition of the silicates can be regulated with the aid of the molar ratio of $SiO_2$ to $Al_2O_3$ in the starting mixture, in the sense that silicates with a lower value for y are obtained according as the molar ratio of $SiO_2$ to $Al_2O_3$ in the starting mixture is chosen higher.

The silicates prepared as described above contain alkali metal and/or alkaline-earth metal ions and organic cations. When suitable exchange methods are used, the alkali metal and alkaline-earth metal ions can be replaced by other cations, such as hydrogen ions or ammonium ions. Organic cations can very conveniently be converted into hydrogen ions by calcining the silicates. The crystalline silicates which are used in the process according to the invention preferably have an alkali metal content of less than 0.1% w, and in particular of less than 0.01% w. When the crystalline silicates are used as the catalyst, they may, if desired, be combined with a natural or synthetic binder material such as bentonite or kaolin.

In the process according to the invention a silicate should be used which has zinc as the promotor. A preferred silicate is one which contains 0.05 to 20% w and particularly 0.1 to 5% w zinc. The incorporation of zinc into the silicate may be performed in various ways, for instance by ion exchange or by impregnation. It is preferred to use in the process a silicate in which the zinc incorporation was performed by impregnating the silicate with an aqueous solution of a zinc salt followed by drying and calcining of the impregnated material.

The process according to the invention can very conveniently be carried out by conducting the feed in upward or downward direction through a vertically mounted reactor, in which a fixed or moving bed of the catalyst concerned is present.

The invention will now be explained with reference to the following example.

EXAMPLE

Three crystalline silicates (silicates A-C) were prepared by heating mixtures of $SiO_2$, $NaAlO_2$, $NaOH$ and $[(C_3H_7)_4N]OH$ in water in an autoclave under autogenous pressure for 24 hours at 150° C. After the reaction mixtures had cooled down the silicates formed were filtered off, washed with water until the pH of the wash water was about 8 and dried for two hours at 120° C. After 1 hour's calcining in air at 500° C. the silicates A-C had the following properties:

(a) thermally stable up to a temperature above 800° C.;

(b) an X-ray powder diffraction pattern substantially equal to the one given in Table B;

(c) after conversion of the silicate into the H-form and after evacuation at $2 \times 10^{-9}$ bar and 400° C. for 16 hours and measured at a hydrocarbon pressure of $8 \times 10^{-2}$ bar and 100° C. the adsorption of n-hexane is 1.2 mmol/g, the adsorption of 2,2-dimethylbutane 0.7 mmol/g and the ratio $$\frac{\text{adsorption of n-hexane}}{\text{adsorption of 2,3-dimethylbutane}} = 1.7;$$

(d) the composition, expressed in moles of the oxides, is the following:
silicate A: 0.030 $M_2O$. 0.030 $Al_2O_3.SiO_2$
silicate B: 0.0038 $M_2O$. 0.0038 $Al_2O_3.SiO_2$
silicate C: 0.0077 $M_2O$. 0.0077 $Al_2O_3.SiO_2$
wherein M=H and Na.

The molar composition of the aqueous mixtures from which the silicates were prepared were given in Table C.

TABLE C

| Silicate | A | B | C |
|---|---|---|---|
| $Na_2O$ | 1.5 | 16 | 8 |
| $Al_2O_3$ | 1 | 1 | 1 |
| $[(C_3H_7)_4N]_2O$ | 6.75 | 72 | 36 |
| $SiO_2$ | 37.5 | 400 | 200 |
| $H_2O$ | 675 | 7200 | 3600 |

The silicates I-III were prepared from the silicates A-C, respectively, by boiling the materials calcined at 500 C. with 1.0 molar $NH_4NO_3$ solution, washing with water, boiling again with 1.0 molar $NH_4NO_3$ solution and washing, drying at 120° C. and calcining at 500° C.

From the silicate I-III as the starting materials the silicates 1-3 were prepared, which contain zinc. The preparation was effected by impregnating samples of the silicates I-III with an aqueous solution of zinc nitrates followed by drying and calcining of the impregnated material to convert the zinc primarily to the oxide.

The silicates 1-3 had the following compositions:
Silicate 1:2% w Zn on silicate I
Silicate 2:2% w Zn on silicate II
Silicate 3:2% w on silicate III The silicates 1-3 and silicate I were tested as catalyst for the preparation of aromatic hydrocarbons and hydrogen from propane. The test was carried out in a 50-ml reactor containing a fixed catalyst bed having a volume of 5 ml consisting of the silicate concerned. Propane was conducted over the catalyst at a temperature of 475° C. and a space velocity of 2 g propane/g silicate/h. The results of these experiments are given in Table D. The following data are included in the table:

$$\text{the activity} = \frac{pbw(\text{total product} - \text{propane in product})}{pbw \text{ total product}} \times 100 \quad (a)$$

$$\text{the aromatics selectivity} = \frac{pbw \text{ aromatic hydrocarbons in product}}{pbw(\text{total product} - \text{propane in product})} \times 100 \quad (b)$$

$$\text{the hydrogen selectivity} = \frac{pbw \text{ hydrogen in product}}{pbw(\text{total product} - \text{propane in product})} \times 100 \quad (c)$$

Table D

| exp. No. | Silicate No. | Pressure bar | Activity | Aromatics selectivity | Hydrogen selectivity |
|---|---|---|---|---|---|
| 1 | 1 | 6 | 33.1 | 39.4 | 2.42 |
| 2 | 1 | 30 | 79.2 | 27.8 | 0.38 |
| 3 | 2 | 6 | 5.1 | 60.5 | 6.81 |
| 4 | 3 | 2 | 24.9 | 39.3 | 3.72 |
| 5 | 1 | 15 | 77.7 | 24.3 | 0.58 |
| 6 | 1 | 6 | 52.8 | 27.1 | 0.76 |

Of the experiments shown in Table D only Exp. No. 1 is an experiment according to the invention. This experiment was carried out at a pressure between 5 and 10 bar using as the catalyst a silicate with zinc as the promoter which silicate had the required y. In this experiment both a high activity and a high aromatics selectivity and hydrogen activity were reached. The experiments 2-6 are outside the scope of the invention and have been included for comparison. In experiment 2 too high a pressure was used, which led to an unacceptably low hydrogen selectivity. In the experiments 3 and 4 either a silicate with too low a y was used or too low a pressure was used, which led in both cases to an unacceptably low activity. In experiments 5 and 6 a silicate was used which would not contain zinc and in experiment 5, in addition, there was too high a pressure, which resulted in both cases in an unacceptably low aromatics selectivity and hydrogen selectivity.

What is claimed is:

1. A process for the preparation of aromatic hydrocarbons and hydrogen, which comprises contacting in a contact zone as feed propane or a hydrocarbon mixture which consists of more than 75%w $C_4$-paraffins and of at least 50%w propane and less than 20% methane and/or ethane at a temperature of from 400°-700° C., a space velocity of from 0.5 to 10 $g.g^{-1}.h^{-1}$ and a pressure of between 5 and 10 bar with a crystalline silicate containing 0.05 to 20% w zinc as the promoter as the catalyst, which silicate is characterized in having the following properties after 1 hour's calcining in air at 500° C.:

(a) thermally stable up to a temperature above 600° C., (b) an X-ray powder diffraction pattern showing, inter alia, the reflections given in Table A.

TABLE A

| Radiation: Cu-K 2θ | Wavelength 0.15418 nm relative intensity |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M |

(c) after conversion of the silicate into the H-form and after evacuation at $2 \times 10^{-9}$ bar and 400° C. for 16 hours and measured at a hydrocarbon pressure of $8 \times 10^{-2}$ bar and 100° C., the adsorption of n-hexane is at least 0.8 mmol/g, the adsorption of 2,2-dimethylbutanes at least 0.5 mmol/g and the ratio $$\frac{\text{adsorption of n-hexane}}{\text{adsorption of 2,2-dimethylbutane}}$$

at least 1.5, (d) the composition, expressed in moles of the oxides, is as follows:

y.(1.0±0.3) $M_{n/2}O$.y. $Al_2O_3.SiO_2$, wherein M=H and/or alkali metal and/or alkaline-earth metal, n is the valency of M and y=0.0065 to 0.1; and recovering an aromatic hydrocarbon mixture and hydrogen-containing gas from said contact zone.

2. A process according to claim 1 wherein said feed is a hydrocarbon mixture consisting of more than 60%w propane.

3. A process according to claim 1 wherein said silicate has an alkali metal content less than 0.1%w.

4. A process according to claim 1 wherein said silicate contains 0.1 to 5%w zinc.

5. A process according to claim 1 wherein said contacting is carried out at a temperature of from 450° to 600° C., a pressure of from 6 to 9 bar and a space velocity of from 0.5 to 10 $g.g^{-1}.h^{-1}$.

* * * * *